(12) United States Patent
Tanino et al.

(10) Patent No.: US 10,580,547 B2
(45) Date of Patent: Mar. 3, 2020

(54) SCINTILLATOR PANEL AND RADIATION DETECTOR

(71) Applicant: TORAY INDUSTRIES, INC., Tokyo (JP)

(72) Inventors: Takahiro Tanino, Otsu (JP); Hideyuki Fujiwara, Otsu (JP); Naohide Itsuki, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/501,984

(22) PCT Filed: Aug. 3, 2015

(86) PCT No.: PCT/JP2015/071931
§ 371 (c)(1),
(2) Date: Feb. 6, 2017

(87) PCT Pub. No.: WO2016/021540
PCT Pub. Date: Feb. 11, 2016

(65) Prior Publication Data
US 2017/0236609 A1    Aug. 17, 2017

(30) Foreign Application Priority Data
Aug. 8, 2014 (JP) .................... 2014-162144

(51) Int. Cl.
*G01T 1/20* (2006.01)
*G21K 4/00* (2006.01)
(Continued)

(52) U.S. Cl.
CPC .............. *G21K 4/00* (2013.01); *G01T 1/20* (2013.01); *G01T 1/202* (2013.01); *G01T 1/2002* (2013.01); *A61B 6/00* (2013.01)

(58) Field of Classification Search
CPC ......... G01T 1/202; G01T 1/2002; G01T 1/20; G21K 4/00; A61B 6/00
See application file for complete search history.

(56) References Cited

U.S. PATENT DOCUMENTS 7,308,074 B2 * 12/2007 Jiang .................... G01T 1/2002
                                                      250/370.09
7,956,598 B2    6/2011 Ariyama
(Continued)

FOREIGN PATENT DOCUMENTS

JP    01191084       8/1989
JP    2004317300    11/2004
(Continued)

OTHER PUBLICATIONS

International Search Report and Written Opinion for International Application No. PCT/JP2015/071931, dated Sep. 8, 2015, 7 pages.

*Primary Examiner* — Kiho Kim
(74) *Attorney, Agent, or Firm* — RatnerPrestia (57) ABSTRACT

Provided is a scintillator panel which can be more easily and conveniently manufactured at a low cost and which has a high luminance and a high sharpness. The scintillator panel according to the present invention includes: a substrate; barrier ribs placed on the substrate; and a phosphor packed into cells separated by the barrier ribs, the phosphor having a porosity of 20% or less and having a grain boundary.

15 Claims, 3 Drawing Sheets

(51) Int. Cl.
*G01T 1/202* (2006.01)
*A61B 6/00* (2006.01)

(56) References Cited

U.S. PATENT DOCUMENTS

| | | | |
|---|---|---|---|
| 8,400,476 B2 | 3/2013 | Iijima | |
| 9,177,683 B2 * | 11/2015 | Iguchi | G01T 1/20 |
| 2004/0185392 A1 * | 9/2004 | Suzuki | G03C 1/12 |
| | | | 430/546 |
| 2006/0202134 A1 * | 9/2006 | Fukui | C09K 11/671 |
| | | | 250/484.4 |
| 2013/0284935 A1 * | 10/2013 | Kaneko | G01T 1/202 |
| | | | 250/361 R |
| 2014/0014846 A1 * | 1/2014 | Kaneko | G01T 1/20 |
| | | | 250/369 |
| 2015/0338529 A1 * | 11/2015 | Svenonius | G01T 1/2002 |
| | | | 250/486.1 |

FOREIGN PATENT DOCUMENTS

| | | | | |
|---|---|---|---|---|
| JP | 2011007552 | 1/2011 | | |
| JP | 2011207937 | 10/2011 | | |
| JP | 2011257339 | 12/2011 | | |
| JP | 5060871 | 10/2012 | | |
| JP | WO 2012161304 A1 * | 11/2012 | | G01T 1/20 |
| JP | 5188148 | 4/2013 | | |
| JP | 2014106022 | 6/2014 | | |
| WO | 2012161304 | 11/2012 | | |

\* cited by examiner

SCINTILLATOR PANEL AND RADIATION DETECTOR

CROSS REFERENCE TO RELATED APPLICATIONS

This application is the U.S. National Phase application of PCT International Application No. PCT/JP2015/071931, filed Aug. 3, 2015, and claims priority to Japanese Patent Application No. 2014-162144, filed Aug. 8, 2014, the disclosures of each of these applications being incorporated herein by reference in their entireties for all purposes.

FIELD OF THE INVENTION

The present invention relates to a scintillator panel, and a radiation detector including the scintillator panel.

BACKGROUND OF THE INVENTION

Radiation images formed using a film have been widely used heretofore at the medical site. However, a radiation image formed using a film presents analog image information. Thus, in recent years, digital-type radiation detectors such as computed radiographies (CR) and flat panel detectors (hereinafter, referred to as "FPD") have been developed. In the FPD, a scintillator panel is used for converting a radiation into visible light. The scintillator panel includes a radiation phosphor. The radiation phosphor emits visible light in response to an applied radiation, and the emitted light is converted into an electric signal by a TFT (thin film transistor) or a CCD (charge-coupled device) to convert information of the radiation into digital image information. However, the FPD has the problem that at the time when the radiation phosphor emits light, visible light is scattered by the radiation phosphor itself, leading to a decrease in S/N ratio.

A method has been proposed in which for reducing influences of scattering of emitted light, a phosphor is separated by barrier ribs, more specifically a phosphor is packed into spaces, i.e. cells, which are separated by preformed barrier ribs. As a method for preforming barrier ribs, etching processing of a silicon wafer, a screen printing method using a glass powder-containing paste, or a photosensitive paste is known (Patent Documents 1 to 4). On the other hand, a method is known in which a single crystal of a phosphor is mechanically processed to form a groove, and barrier ribs are embedded in this groove (Patent Document 5).

PATENT DOCUMENTS

Patent Document 1: Japanese Patent Laid-open Publication No. 5-60871
Patent Document 2: Japanese Patent Laid-open Publication No. 5-188148
Patent Document 3: Japanese Patent Laid-open Publication No. 2011-007552
Patent Document 4: International Publication No. WO 2012/161304
Patent Document 5: Japanese Patent Laid-open Publication No. 2004-317300

SUMMARY OF THE INVENTION

However, a method in which a phosphor is packed into cells separated by preformed barrier ribs has the problem that scattering of emitted light cannot be sufficiently reduced, and thus the amount of emitted light absorbed in the barrier ribs increases, leading to a reduction in luminance of a scintillator panel. On the other hand, a single crystal phosphor is more desirable for suppressing scattering of emitted light, but operations for forming a groove in a single crystal of a phosphor are delicate, so that not only an extremely long time is required, but also a loss occurs in the single crystal of a phosphor due to processing, and therefore the luminance of the scintillator panel is not sufficient while a very high cost is required.

An object of the present invention is to provide a scintillator panel which can be more easily and conveniently manufactured at a low cost and which has a high luminance and a high sharpness.

The object is achieved by any of the following technical means.

(1) A scintillator panel including: a substrate; barrier ribs placed on the substrate; and a phosphor packed into cells separated by the barrier ribs, the phosphor being a compound selected from the group consisting of CsI:Tl, NaI:Tl and SrI2:Eu, the phosphor having a porosity of 20% or less and having a grain boundary.

(2) The scintillator panel according to (1), wherein the phosphor has a porosity of 0.1% or more.

(3) The scintillator panel according to (1) or (2), wherein the phosphor has an average particle size of 1 to 200 μm.

(4) The scintillator panel according to any one of (1) to (3), wherein the barrier rib includes an inorganic substance, and the barrier rib has a porosity of 25% or less.

(5) The scintillator panel according to any one of (1) to (4), wherein the barrier rib has a Young's modulus of 10 GPa or more.

(6) The scintillator panel according to any one of (1) to (5), wherein the barrier rib contains glass as a main component.

(7) The scintillator panel according to any one of (1) to (6), wherein the scintillator panel includes a reflecting layer between the barrier rib and the phosphor, and the reflecting layer contains a metal oxide as a main component.

(8) The scintillator panel according to any one of (1) to (7), wherein the scintillator panel includes a light shielding layer between the barrier rib and the phosphor, and the light shielding layer contains a metal as a main component.

(9) The scintillator panel according to (7) or (8), wherein the scintillator panel includes a protective layer between the reflecting layer and the phosphor or between the light shielding layer and the phosphor.

(10) The scintillator panel according to any one of (1) to (9), which is manufactured by a method including the step of press-packing a phosphor selected from the group consisting of CsI:Tl, NaI:Tl and SrI2:Eu in cells separated by barrier ribs.

(11) The scintillator panel according to (10), wherein the pressure in the press-packing is 10 to 1000 MPa.

(12) The scintillator panel according to (10) or (11), wherein, the temperature in the press-packing is 0 to 630° C.

(13) The scintillator panel according to any one of (10) to (12), wherein the press-packing is performed under vacuum.

(14) The scintillator panel according to any one of (10) to (13), wherein the phosphor that is subjected to the press-packing step is in the form of a thin-film.

(15) The scintillator panel according to (14), wherein the phosphor in the form of a thin-film is obtained by press-molding a phosphor powder.

(16) A radiation detector including the scintillator panel according to any one of (1) to (15).

According to the present invention, a scintillator panel having a high luminance and a high sharpness can be more easily and conveniently prepared at a low cost.

DETAILED DESCRIPTION OF EMBODIMENTS OF THE INVENTION

Hereinafter, a specific configuration of a scintillator panel according to embodiments of the present invention will be described with reference to the drawings, but the present invention is not limited thereto.

Figure 1:
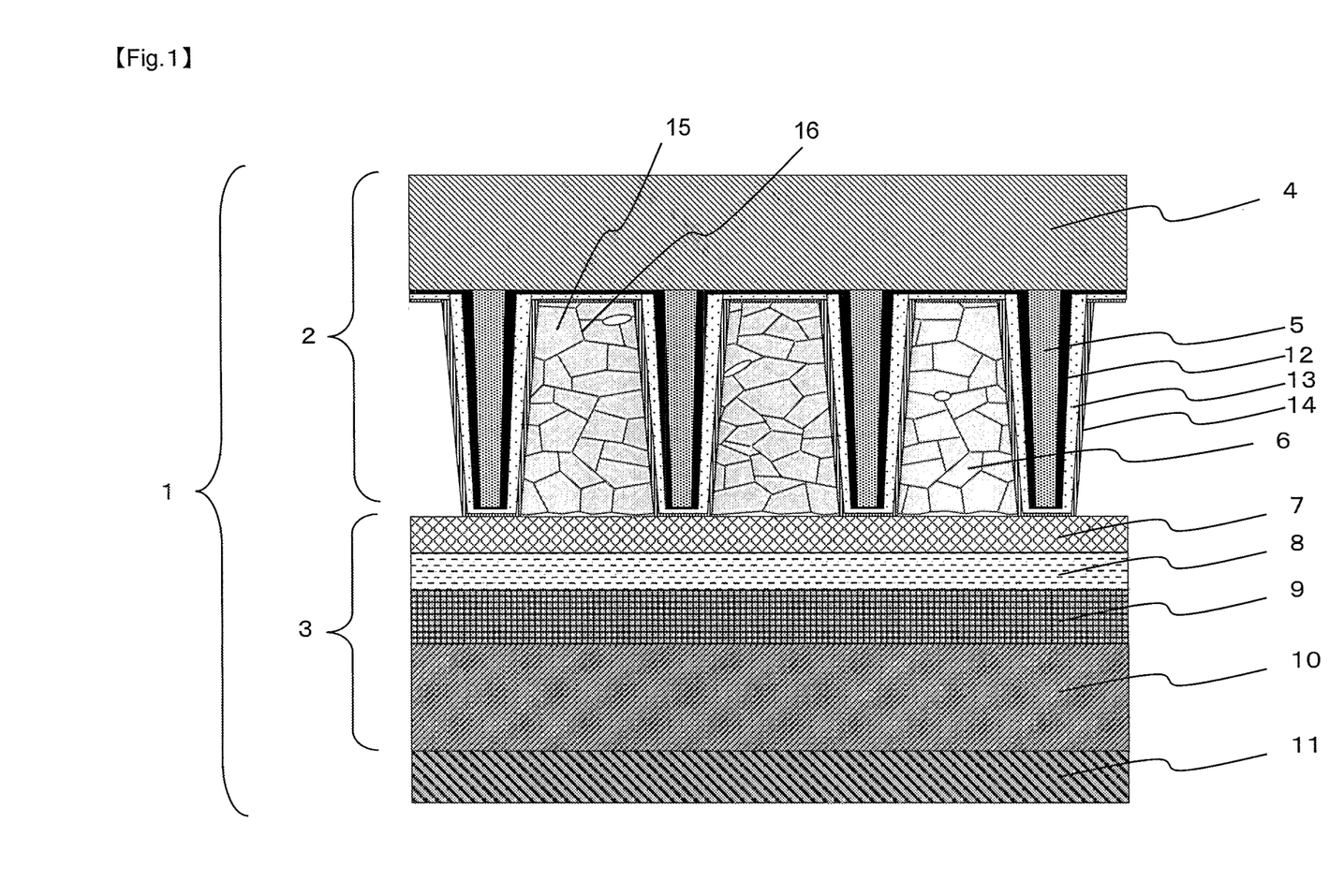
FIG. 1 is a sectional view schematically showing a configuration of a radiation detector including a scintillator panel according to an embodiment of the present invention.
Figure 2:
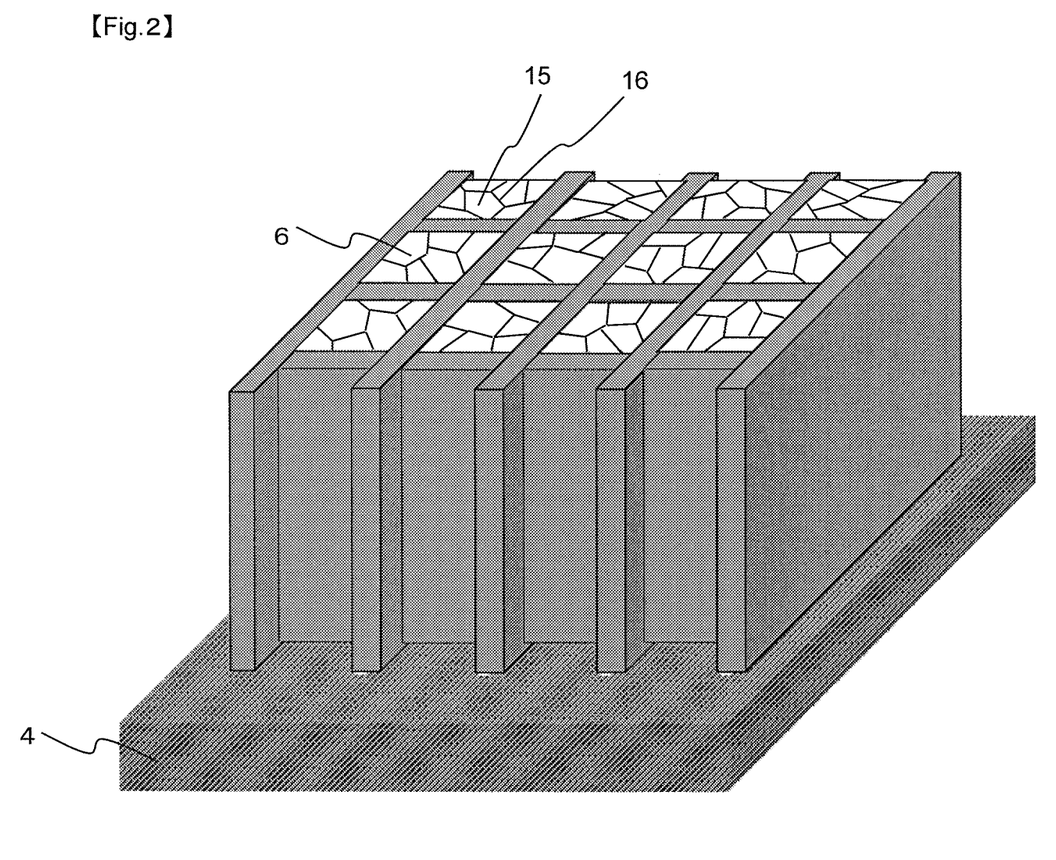
FIG. 2 is a perspective view schematically showing a configuration of the scintillator panel according to an embodiment of the present invention.

FIG. 1 is a sectional view schematically showing a configuration of a radiation detector including the scintillator panel according to an embodiment of the present invention. FIG. 2 is a perspective view schematically showing a configuration of the scintillator panel according to an embodiment of the present invention. A radiation detector 1 includes a scintillator panel 2, an output substrate 3 and a power supply unit 11. The scintillator panel 2 includes a phosphor layer 6, i.e. a phosphor, and the phosphor absorbs energy of an incident radiation, and emits an electromagnetic wave having a wavelength ranging from 300 nm to 800 nm, i.e. an electromagnetic wave (light) ranging from ultraviolet light to infrared light with visible light at the center.

The scintillator panel 2 includes: a substrate 4; barrier ribs 5 for forming separated spaces, i.e. cells, on the substrate 4; light shielding layers 12 formed on surfaces of the barrier ribs 5 and areas of the substrate 4, which are not provided with the barrier ribs; reflecting layers 13; protective layers 14; phosphor crystal 15; discontinuous boundary surface generated between crystals of the phosphor 16; and phosphor layers 6 including a phosphor packed into the spaces separated by the barrier ribs 5.

The output substrate 3 includes on a substrate 10 a photoelectric conversion layer 8 and an output layer 9 in which pixels each composed of a photoelectric conversion element and a TFT are two-dimensionally formed. The radiation detector 1 is obtained by bonding or adhering the light emitting surface of the scintillator panel 2 and the photoelectric conversion layer 8 of the output substrate 3 to each other with a barrier layer 7 interposed therebetween, the barrier rib layer 8 being composed of a polyimide resin etc. When light emitted from the phosphor layer 6 arrives at the photoelectric conversion layer 8, photoelectric conversion is performed at the photoelectric conversion layer 8, and an electric signal is outputted through the output layer 9. In the scintillator panel according to an embodiment of the present invention, the cells are separated by barrier ribs, and therefore when the size and pitch of the pixel of the photoelectric conversion element disposed in a grid-like shape are made equal to the size and pitch of the cell of the scintillator panel, each pixel of the photoelectric conversion element can be associated with each cell of the scintillator panel.

The scintillator panel according to an embodiment of the present invention includes: a substrate; barrier ribs placed on the substrate; and a phosphor packed into cells separated by the barrier ribs, the phosphor having a porosity of 20% or less and having a grain boundary.

The substrate is a flat-shaped support on which barrier ribs are placed. The material of the substrate is, for example, a polymer, a ceramic, a semiconductor, a metal or glass, which is permeable to a radiation. The polymer compound is, for example, polyester, cellulose acetate, polyamide, polyimide, polycarbonate or a carbon fiber-reinforced resin. The ceramic is, for example, alumina, aluminum nitride, mullite, steatite, silicon nitride or silicon carbide. The semiconductor is, for example, silicon, germanium, gallium arsenide, gallium phosphorus or gallium nitrogen. The metal is, for example, aluminum, iron, copper or metal oxides. The glass is, for example, quartz, borosilicate glass or chemically reinforced glass.

The thickness of the substrate is preferably 1 mm or less for suppressing absorption of a radiation by the substrate.

The reflectance of the substrate is preferably 90% or more. When the reflectance is 90% or more, the luminance of the scintillator panel is improved. The substrate having a reflectance of 90% or more is, for example, a white PET film that is used as a reflecting plate in a liquid crystal display. Here, the reflectance is a SCI reflectance at a wavelength of 530 nm, which is measured using a spectral colorimeter (e.g. CM-2600d; manufactured by KONICA MINOLTA, INC.).

Figure 3:
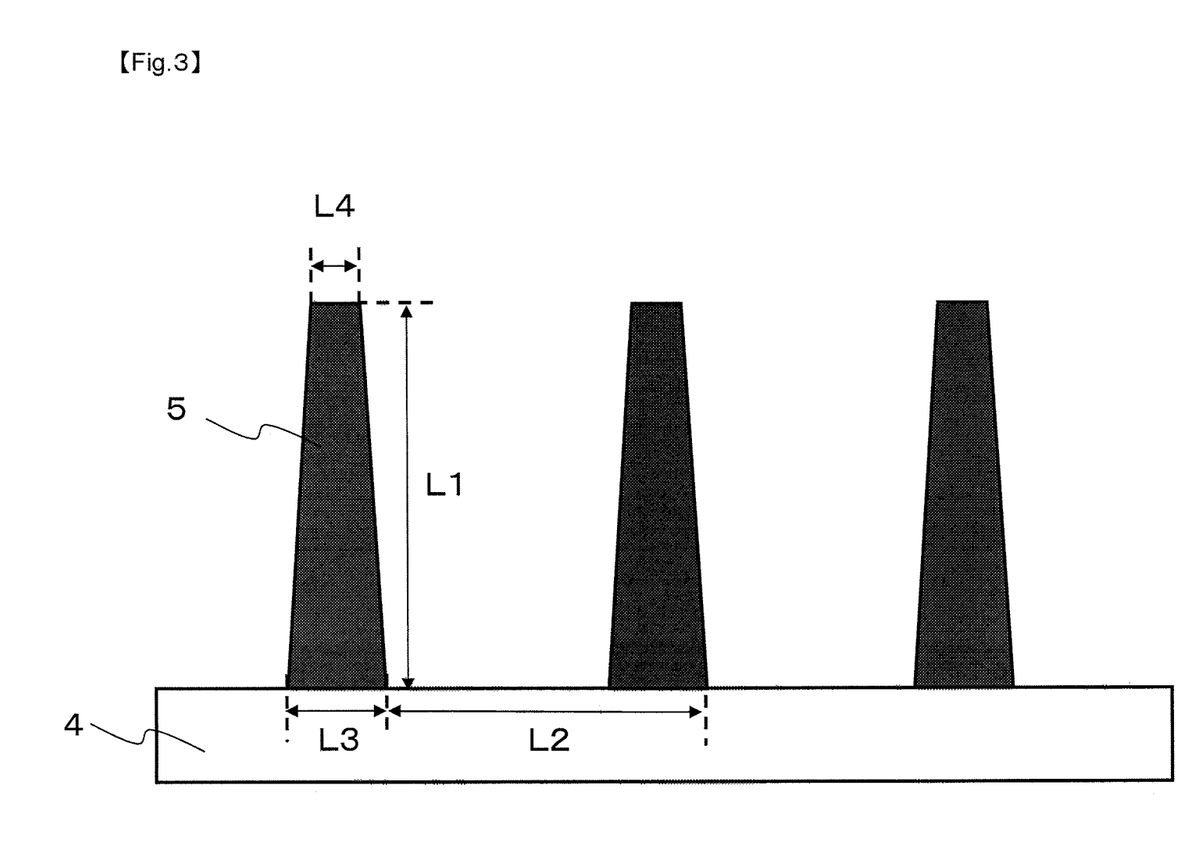
FIG. 3 is a sectional view schematically showing the configuration of the scintillator panel according to an embodiment of the present invention.

FIG. 3 is a sectional view schematically showing the configuration of the scintillator panel according to an embodiment of the present invention.

The height L1 of the barrier rib 5 is preferably 100 to 3000 μm, more preferably 160 to 1000 μm. When the height L1 is more than 3000 μm, light emitted by the phosphor itself may be markedly absorbed, leading to a reduction in luminance. On the other hand, when the height L1 is less than 100 μm, the amount of the phosphor which can be packed may decrease, leading to a reduction in luminance of the scintillator panel.

The interval L2 between adjacent barrier ribs is preferably 30 to 1000 μm. When the interval L2 is less than 30 μm, it is apt to be difficult to pack the phosphor in the cell. On the other hand, when the interval L2 is more than 1000 μm, the sharpness of the scintillator panel may be reduced.

The bottom part width L3 of the barrier rib is preferably 5 to 150 μm, more preferably 10 to 100 μm. When the bottom part width L3 is less than 5 μm, so that pattern defects easily occur. On the other hand, when the bottom part width L3 is more than 150 μm, the amount of the phosphor which can be packed may decrease, leading to a reduction in luminance of the scintillator panel.

The top part width L4 of the barrier rib is preferably 5 to 80 μm. When the top part width L4 is less than 5 μm, the strength of the barrier rib is reduced, so that pattern defects easily occur. On the other hand, when the top part width L4 is more than 80 μm, a region where light emitted by the phosphor can be extracted may be narrowed, leading to a reduction in luminance of the scintillator panel.

The aspect ratio (L1/L3) of the height L1 of the barrier rib to the bottom part width L3 of the barrier rib is preferably 1.0 to 50.0. When the aspect ratio (L1/L3) of the barrier rib increases, a space per pixel separated by the barrier rib becomes wider, so that a larger amount of the phosphor can be packed in the space.

The aspect ratio (L1/L2) of the height L1 of the barrier rib to the interval L2 between barrier ribs is preferably 0.5 to 5.0, more preferably 1.0 to 5.0. When the aspect ratio (L1/L2) of the barrier rib increases, a pixel is finely separated, and a larger amount of the phosphor can be packed in a space per pixel.

The height L1 of the barrier rib and the interval L2 between adjacent barrier ribs can be measured in the following manner: a cross-section vertical to a substrate is exposed by a polishing apparatus such as a cross section polisher, and the cross-section is observed with a scanning electron microscope (e.g. S2400; manufactured by Hitachi, Ltd.). Here, L3 is the width of the barrier rib at a contact part between the barrier rib and the substrate. L4 is the width of the topmost part of the barrier rib.

Preferably, the barrier rib is composed of an inorganic substance for improving the strength and heat resistance of the barrier rib. Here, the inorganic substance is a compound composed of some simple carbon compound (e.g. an allotrope of carbon such as graphite or diamond) and elements other than carbon. The term "composed of an inorganic substance" does not exclude existence of components other than an inorganic substance in the strict sense, and existence of components other than an inorganic substance, such as impurities contained in the inorganic substance serving as a raw material, and impurities entering during manufacturing of the barrier rib, is acceptable.

The porosity of the barrier rib is preferably 25% or less. When the porosity is more than 25%, the strength of the barrier rib is apt to be insufficient. The porosity of the barrier rib can be measured in the following manner: an image of a cross-section of the barrier rib, which is vertical to a substrate using a scanning electron microscope, a solid portion and a void portion in the barrier rib are distinguished from each other by binarization, and the ratio of the void portion is determined by image analysis.

The Young's modulus of the barrier rib is preferably 10 GPa or more. When the Young's modulus is 10 GPa or more, the strength of the barrier rib is improved, so that the barrier rib is harder to damage at the time of packing the phosphor. The Young's modulus of the barrier rib can be measured by a nanoindentation method that is a micro-region-push-in method.

Preferably, the barrier rib contains glass as a main component. Here, the glass is an inorganic amorphous solid containing a silicate. When the main component of the barrier rib is glass, the strength and heat resistance of the barrier rib are improved, so that the barrier rib is harder to rupture at the time of packing the phosphor. The phrase "containing glass as a main component" means that glass constitutes 50 to 100% by mass of materials for forming the barrier rib.

In the scintillator panel according to an embodiment of the present invention, a phosphor selected from the group consisting of CsI:Tl, NaI:Tl and SrI2:Eu is packed in cells separated by barrier ribs. Here, CsI:Tl is cesium iodide doped with thallium as a dopant. Similarly, NaI:Tl is sodium iodide doped with thallium as a dopant, and SrI2:Eu is strontium iodide doped with europium as a dopant. Preferably, the phosphor does not substantially contain an organic substance such as a binder resin. Here, the phrase "the phosphor does not substantially contain an organic substance" means that the content of an organic substance in the phosphor packed in the barrier rib is 1% by weight or less. The phosphor is composed preferably only of a phosphor selected from the group consisting of CsI:Tl, NaI:Tl and SrI2:Eu, but may contain other phosphor dopants or impurities.

The porosity of the porosity of the phosphor packed in the cells should be 20% or less, and is preferably 10% or less, more preferably 5% or less. The porosity of the phosphor packed in the cells is preferably 0.1% or more. When the porosity of the phosphor is 20% or less, the packed amount of the phosphor increases, and light scattering in the phosphor is suppressed, so that the luminance and sharpness of the scintillator panel are improved. On the other hand, when the porosity of phosphor is 0.1% or more, the phosphor tends to include a proper grain boundary, so that the luminance of the scintillator panel is easily improved. The porosity of the packed phosphor can be measured by the same method as that used for measuring the porosity of the barrier rib. For minimizing a measurement error, the analyzed range of the image of a cross-section of the phosphor, which is taken using a scanning electron microscope, is prevented from including the barrier rib, the substrate or the like, image analysis is performed for each of 10 randomly selected cells, the analysis results are averaged, and the average thus obtained is defined as a porosity of the phosphor.

The phosphor packed in the cells should have a grain boundary. Here, the grain boundary is a discontinuous boundary surface generated between a plurality of crystals of the phosphor. When the phosphor packed in the cells has a grain boundary, the luminance and sharpness of the scintillator panel is improved. Although the mechanism thereof is not clear, it is thought that the grain boundary serves as a waveguide because an X-ray light emission image of a phosphor having a grain boundary shows that the grain boundary portion particularly intensely emits light. It is thought that due to existence of a grain boundary at a surface of the phosphor layer, which faces the output substrate, emitted light is easily extracted efficiently from the phosphor to the output substrate side through the grain boundary. Presence/absence of a grain boundary in the phosphor packed in the cell can be determined by observing an image of a cross-section of the phosphor, which is vertical to the substrate, using a scanning electron microscope. It may be difficult to discriminate the outline of the grain shape with a usual scanning microscope, but the outline of the grain shape can be clearly discriminated by using an EBSD (electron back scatter diffraction patterns) method.

The average particle size of the phosphor packed in the cell is preferably 1 to 200 μm. When the average particle size of the phosphor is less than 1 μm, emitted light may be excessively scattered, leading to a reduction in luminance of the scintillator panel. On the other hand, when the average particle size of the phosphor is more than 200 μm, the distribution of grain boundaries and voids becomes inappropriate, leading to a reduction in luminance of the scintillator panel. The particle size is more preferably 10 to 100 μm, still more preferably 20 to 60 μm.

The average particle size of the phosphor packed in the cell is determined in the following manner: an image of a cross-section of the phosphor at a cross-section of the scintillator panel, which is vertical to the substrate, is taken using a scanning electron microscope, and for three randomly selected cells, each of individual single crystals of the phosphor, which are separated by grain boundaries, is regarded as one particle, and the image is analyzed using image analysis software for all particles in the cell. Regions separated by grain boundaries can be more clearly observed by obtaining an image using an EBSD method as in the case of determination of presence/absence of a grain boundary.

In the present invention, the shape of the phosphor packed in the cell is preferably granular. An image of a cross-section of the phosphor at a cross-section of the scintillator panel is taken using a scanning electron microscope, and for randomly selected 10 crystals among crystals of the phosphor, which are separated grain boundaries, the long diameter and the short diameter of the cross-section are measured, the long diameter is divided by the short diameter, and the values thus obtained for the 10 crystals are averaged. When the obtained average is 10 or less, the phosphor is granular. When the phosphor is granular, degradation of the phosphor layer tends to more hardly occur because impurities such as moisture are harder to enter the crystal as compared to a nongranular phosphor such as a columnar-crystal phosphor.

Preferably, the scintillator panel according to the present invention includes a reflecting layer, which contains a metal oxide, between the barrier rib and the phosphor layer. Here, the phrase "including the reflecting layer between the barrier rib and the phosphor layer" means, for example, a state in which the reflecting layer is formed on surfaces of the substrate and the barrier rib, which are in contact with the phosphor layer. Preferably, the reflecting layer contains a metal oxide as a main component. The phrase "containing a metal oxide as a main component" means that the ratio of a metal oxide to the reflecting layer is 50% by volume or more. When the scintillator panel includes the reflecting layer, which contains a metal oxide, between the barrier rib and the phosphor layer, the reflectance of each of the substrate and the barrier rib placed on the substrate can be made suitable.

The average thickness of the reflecting layer is preferably 5 to 20 µm. Here, the average thickness of the reflecting layer is a value obtained by dividing the area of 10 reflecting layers, which are randomly selected on a cross-section of the scintillator panel vertical to the substrate, by the formation length of the reflecting layer, and the formation length of the reflecting layer is a total of the lengths of the portions where the reflecting layer and the under-layer thereof (barrier rib or light shielding etc.) are in contact with each other on the cross-sections of the 10 cells. More specifically, the average thickness of the reflecting layer can be calculated by passing through a process in which a cross-section of the scintillator panel vertical to the substrate is exposed by a polishing apparatus, the cross-section is observed with a scanning electron microscope, and image processing is performed.

When the average thickness of the reflecting layer is less than 5 µm, the reflectance may be insufficient. On the other hand, when the average thickness of the reflecting layer is more than 20 µm, the volume of the phosphor layer may be insufficient, leading to a reduction in luminance of the scintillator panel.

The metal oxide contained in the reflecting layer is preferably a compound selected from the group consisting of titanium oxide, zirconium oxide and aluminum oxide for achieving a more preferred reflectance. Preferably, the reflecting layer formed of such a metal oxide has a suitable reflectance.

Preferably, the scintillator panel in an inspection apparatus for a large structure according to the present invention includes the light shielding layer, which contains a metal, between the barrier rib and the phosphor layer. When the scintillator panel includes the light shielding layer, which contains a metal, between the barrier rib and the phosphor layer, leakage of scintillation light to the adjacent cell can be inhibited. Preferably, the light shielding layer contains a metal as a main component. The phrase "containing a metal as a main component" means that the ratio of a metal to the light shielding layer is 50% by volume or more.

The method for forming the light shielding layer is, for example, a vacuum deposition method such as a vacuum vapor deposition method, a sputtering method or a CVD method, a plating method, a paste application method or a spraying method using a spray. The metal contained in the light shielding layer is, for example, aluminum, chromium, silver, tungsten, molybdenum or lead. The average thickness of the light shielding layer is preferably 20 to 1000 nm. When the average thickness of the light shielding layer is less than 20 nm, the effect of suppressing leakage of scintillation light and the effect of absorbing an X ray are apt to be insufficient. On the other hand, when the average thickness of the light shielding layer is more than 1000 nm, the volume of the phosphor layer may be insufficient, leading to a reduction in luminance of the scintillator panel. The average thickness of the light shielding layer can be calculated by the same method as that used for calculating the average thickness of the reflecting layer.

When both the light shielding layer and the reflecting layer are formed between the barrier rib and the phosphor layer, it is preferable to form the reflecting layer on the light shielding layer for avoiding a situation in which the reflectance becomes insufficient due to absorption of light by the light shielding layer.

Preferably, the protective layer is formed so that the light shielding layer and the reflecting layer do not fall off at the time when the phosphor is packed into the cell. When the light shielding layer and the protective layer are formed, the protective layer is formed between the light shielding layer and the phosphor layer after formation of the light shielding layer. When the reflecting layer and the protective layer are formed, the protective layer is formed between the reflecting layer and the phosphor layer after formation of the reflecting layer. When all of the light shielding layer, the reflecting layer and the protective layer are formed, it is preferable to form the light shielding layer, the reflecting layer and the protective layer in this order. The material of the protective layer is, for example, a substance which is dense and strong even when being thin and which has low reactivity, such as glass, $SiO_2$ or resin. When a large thermal load is applied in a post-treatment step, it is preferable to use an inorganic substance such as glass or $SiO_2$. On the other hand, in the case of an organic substance, polyparaxylylene as a resin is more preferable because it has low reactivity.

The method for forming the protective layer is, for example, a vacuum deposition method, a plating method and a spraying method, and a vacuum deposition method is preferable for forming a denser film. When the thickness of the film is large, the amount of the composition containing an inorganic material, which is packed in cells, decreases, and therefore it is preferable that the film is formed in the smallest thickness within such a range that the light shielding layer and the reflecting layer do not fall off. In the case of polyparaxylylene, it is preferable that the film is formed in a thickness of 1 to 5 µm.

Preferably, the method for manufacturing a scintillator panel according to the present invention includes the step of press-packing a phosphor in cells separated by barrier ribs.

The press-packing is a method in which a pressure is applied to a phosphor to pack the phosphor in cells separated by barrier ribs. A phosphor selected from the group consisting of CsI:Tl, NaI:Tl and SrI2:Eu can be packed into barrier ribs uniformly and with a low porosity even under mild conditions of a relatively low temperature and low pressure because the phosphor has such a unique nature that crystals are plastically even at a low temperature and low pressure. On the other hand, other phosphors are very difficult to press-pack because they have the problem that the phosphor is not plastically deformed, and thus the porosity of the phosphor layer after packing of the phosphor into the barrier rib cannot be reduced to 20% or less, that the phosphor itself is degraded under pressure, that a high temperature and high pressure is required for high-density packing, and therefore deformation or rupture of barrier ribs cannot be avoided, and so on.

The method for applying a pressure to the phosphor is, for example, uniaxial pressing, cold isostatic pressing or hot isostatic pressing.

The pressure in press-packing is preferably 10 to 1000 MPa, more preferably 50 to 400 MPa. When the pressure in press-packing is less than 10 MPa, plastic deformation of the phosphor may be so insufficient that the porosity does not decrease, and thus emitted light is excessively scattered, leading to a reduction in luminance of the scintillator panel. On the other hand, when the pressure in press-packing is more than 1000 MPa, the phosphor may be single-crystallized, leading to a reduction in luminance of the scintillator panel, and deformation or rupture of barrier ribs easily occurs.

The temperature in press-packing is preferably 0 to 630° C. When the temperature in press-packing is higher than 630° C., the phosphor may be single-crystallized, leading to a reduction in luminance of the scintillator panel, and deformation or rupture of barrier ribs easily occurs. The temperature in press-packing is more preferably 500° C. or lower, still more preferably 300° C. or lower.

Preferably, press-packing is performed under vacuum. When press-packing is performed under vacuum, the porosity of the phosphor layer is easily reduced. The method for performing packing under vacuum is not particularly limited, and may be a method in which pressing is performed while a pressing mechanism unit of a press machine is kept under vacuum, or a method in which an object to be pressed is put in a plastic bag or a metal thin-film container sealed and molded in the form of a bag, the inside of the bag is then evacuated into vacuum, and the bag is then pressed. Methods for applying a pressure to an object in the form of a bag are classified into several methods according to a medium to be used, a heating temperature, or the like, and examples thereof include a CIP method, a WIP method and a HIP method. Here, the CIP method (cold isostatic pressing method) is a method in which a liquid such as water is used as a medium, and heating is not performed; the WIP method (warm isostatic pressing method) is a method in which a liquid such as water or silicon oil is used as a medium, and heating is performed at 15 to 200° C.; and the HIP method (hot isostatic pressing method) is a method in which an argon gas or nitrogen gas is used as a medium, and heating is performed at 15 to 2500° C.

The phosphor to be press-packed is preferably in the form of a powder or thin film (sheet), more preferably in the form of a thin film. The method for obtaining a phosphor in the form of a thin film is preferably a method in which a powdered phosphor is press-molded. When the phosphor is formed into a thin film, then disposed on the opening surfaces of cells, and press-packed, the porosity of the phosphor layer can be further reduced.

After the phosphor is packed, an excess composition may be wiped off with a solvent etc., or mechanically abraded. When the thickness of the excess phosphor is large, emitted light is easily scattered in the horizontal direction of the display member. Therefore, it is preferable that the thickness of the composition is adjusted during packing so that the height of the packed composition is equivalent to the height of the barrier rib, or the excess composition is wiped off with a solvent etc. after packing, or removed by abrading after packing.

As a method for forming the barrier rib, a known method can be used, but a photosensitive paste method is preferable because shape control is easy.

For example, barrier ribs containing glass as a main component can be formed through an application step of applying a photosensitive paste, contains a glass powder, to a surface of a base material to obtain an applied film; a pattern forming step of exposing and developing the applied film to obtain a pre-firing pattern of the barrier rib; and a firing step of firing a pattern to obtain a barrier rib pattern. For manufacturing barrier ribs containing glass as a main component, a glass powder should constitute 50 to 100% by mass of inorganic components contained in the glass powder-containing paste that is used in the application step.

The glass powder contained in the glass powder-containing paste is preferably a powder of glass that is softened at a firing temperature, more preferably a powder of low-softening-point glass having a softening temperature of 700° C. or lower.

The softening temperature can be determined by extrapolating a heat absorption end temperature at an endothermic peak by a tangent method from a DTA curve obtained by measuring a sample using a differential thermal analyzer (e.g. Differential thermogravimetric analyzer TG8120; manufactured by Rigaku Corporation). More specifically, first an inorganic powder as a measurement sample is measured with the temperature elevated at a rate of 20° C./minute from room temperature using a differential thermal analyzer, so that a DTA curve is obtained. In this measurement, an alumina powder is used as a standard sample. From the obtained DTA curve, a softening point Ts is determined by extrapolating a heat absorption end temperature at an endothermic peak by a tangent method. The softening point Ts can be defined as a softening temperature.

For obtaining low-softening-point glass, a metal oxide selected from the group consisting of lead oxide, bismuth oxide, zinc oxide and an oxide of an alkali metal, each of which is a compound effective for lowering the softening point of glass, can be used, but it is preferable to adjust the softening temperature of glass using an oxide of an alkali metal. Here, the alkali metal is a metal selected from the group consisting of lithium, sodium and potassium.

The ratio of the alkali metal oxide to the low-softening-point glass is preferably 2 to 20% by mass. When the ratio of the alkali metal oxide is less than 2% by mass, the softening temperature increases, and thus it is necessary to carry out the firing step at a high temperature, so that defects easily occur in barrier ribs. On the other hand, when the ratio of the alkali metal oxide is more than 20% by mass, the viscosity of glass excessively decreases in the firing step, so that the shape of the resulting grid-like post-firing pattern is easily strained.

Preferably, the low-softening-point glass contains 3 to 10% by mass of zinc oxide for the glass to have an optimum viscosity at a high temperature. When the ratio of zinc oxide to the low-softening-point glass is less than 3% by mass, the viscosity at a high temperature increases. On the other hand, when the content of zinc oxide is more than 10% by mass, the manufacturing cost of the low-softening-point glass increases.

Preferably, the low-softening-point glass contains a metal oxide selected from the group consisting of silicon oxide, boron oxide, aluminum oxide and an oxide of an alkali earth metal for adjusting stability, crystallinity, transparency, a refractive index or thermal expansion characteristics. Here, the alkali earth metal is a metal selected from the group consisting of magnesium, potassium, barium and strontium.

One example of the composition range for preferred low-softening-point glass is shown below.
Alkali metal oxide: 2 to 20% by mass
Zinc oxide: 3 to 10% by mass
Silicon oxide: 20 to 40% by mass
Boron oxide: 25 to 40% by mass
Aluminum oxide: 10 to 30% by mass
Alkali earth metal oxide: 5 to 15% by mass The particle size of an inorganic powder including a glass powder can be measured using a particle size distribution analyzer (e.g. MT3300; manufactured by NIKKISO Co., Ltd.). More specifically, an inorganic powder is added in a water-filled sample chamber of a particle size distribution analyzer, and subjected to an ultrasonic treatment for 300 seconds, and the particle size of the inorganic powder is then measured.

The 50%-volume average particle size (hereinafter, referred to as "D50") of the low-softening-point glass powder is preferably 1.0 to 4.0 μm. When the volume average particle size D50 is less than 1.0 μm, the glass powder is aggregated, and thus uniform dispersibility is no longer obtained, so that flow stability of the paste is deteriorated. On the other hand, when the volume average particle size D50 is more than 4.0 μm, the surface irregularity of a post-firing pattern obtained in the firing step becomes larger, so that the barrier rib may be easily ruptured later.

The glass powder-containing paste may contain, in addition to low-softening-point glass, high-softening-point, glass having a softening temperature of 700° C. or higher, or ceramic particles such as those of silicon oxide, aluminum oxide, titanium oxide or zirconium oxide as a filler for control of the shrinkage ratio of a grid-like pattern in the firing step, and retention of the shape of the barrier rib that is finally obtained. The ratio of the filler to all the inorganic components is preferably 50% by mass or less for preventing a reduction in strength of the barrier rib due to hindrance of sintering of the glass powder. The volume average particle size D50 of the filler is preferably the same as that of the low-softening-point glass powder.

In a photosensitive glass powder-containing paste, the refractive index n1 of the glass powder and the refractive index n2 of the organic component satisfy the relationship of preferably $-0.1<n1-n2<0.1$, more preferably $-0.01 \le n1-n2 \le 0.01$, still more preferably $-0.005 \le n1-n2 \le 0.005$ for suppressing light scattering during exposure to form a precise pattern. The refractive index of the glass powder can be appropriately adjusted according to the composition of a metal oxide contained in the glass powder.

The refractive index of the glass powder can be measured by a Becke line detection method. The refractive index of the organic component can be determined by measuring a coating film composed of the organic component by ellipsometry. More specifically, the refractive index (ng) to light having a wavelength of 436 nm (g-ray) at 25° C. can be defined as n1 for the glass powder and n2 for the organic component.

The photosensitive organic component contained in the photosensitive glass powder-containing paste is, for example, a photosensitive monomer, a photosensitive oligomer or a photosensitive polymer. Here, the photosensitive monomer, photosensitive oligomer or photosensitive polymer is a monomer, oligomer of polymer which causes a reaction such as photo-crosslinking or photo-polymerization to change its chemical structure when irradiated with active light.

The photosensitive monomer is preferably a compound having an active carbon-carbon unsaturated double bond. The compound is, for example, a compound having a vinyl group, an acryloyl group, a methacryloyl group or an acrylamide group, and a polyfunctional acrylate compound or a polyfunctional methacrylate compound is preferable for increasing the density of photo-crosslinking to form a precise pattern.

The photosensitive oligomer or photosensitive polymer is an oligomer or polymer having an active carbon-carbon unsaturated double bond and having a carboxyl group. The oligomer or polymer is obtained by, for example, a carboxyl group-containing monomer such as acrylic acid, methacrylic acid, itaconic acid, crotonic acid, maleic acid, fumaric acid, vinyl acetic acid or an acid anhydride thereof, a methacrylic acid ester, an acrylic acid ester, styrene, acrylonitrile, vinyl acetate or 2-hydroxy acrylate. The method for introducing an active carbon-carbon unsaturated double bond into an oligomer or polymer is, for example, a method in which chloride acrylate, chloride methacrylate, allyl chloride, an ethylenically unsaturated compound having a glycidyl group or an isocyanate group, or a carboxylic acid such as maleic acid is reacted with a mercapto group, an amino group, a hydroxyl group or a carboxyl group in the oligomer or polymer.

By using a photosensitive monomer or photosensitive oligomer having a urethane bond, a glass powder-containing paste which is capable of relaxing stress in the initial stage of the firing step and which hardly causes damage to a pattern in the firing step.

The photosensitive glass powder-containing paste may contain a photo-polymerization initiator as necessary. Here, the photo-polymerization initiator is a compound which generates a radical when irradiated with active light. The photo-polymerization initiator is, for example, benzophenone, methyl o-benzoylbenzoate, 4,4-bis(dimethylamino)benzophenone, 4,4-bis(diethylamino)benzophenone, 4,4-dichlorobenzophenone, 4-benzoyl-4-methyldiphenylketone, dibenzylketone, fluorenone, 2,2-dimethoxy-2-phenylacetophenone, 2-hydroxy-2-methylpropiophenone, thioxanthone, 2-methylthioxanthone, 2-chlorothioxanthone, 2-isopropylthioxanthone, diethylthioxanthone, benzyl, benzyl methoxyethyl acetal, benzoin, benzoin methyl ether, benzoin butyl ether, anthraquinone, 2-t-butylanthraquinone, anthrone, benzanthrone, dibenzosuberone, methylene anthrone, 4-azidebenzalacetophenone, 2,6-bis(p-azidebenzylidene)cyclohexanone, 2,6-bis(p-azidebenzylidene)-4-methylcyclohexanone, 1-phenyl-1,2-butadione-2-(O-methoxycarbonyl)oxime, 1-phenyl-1,2-propanedione-2-(O-ethoxycarbonyl)oxime, 1,3-diphenylpropanetrione-2-(O-ethoxycarbonyl)oxime, 1-phenyl-3-ethoxypropanetrione-2-(O-benzoyl)oxime, Michler's ketone, 2-methyl-1-[4-(methylthio)phenyl]-2-morpholino-1-propanone, 2-benzyl-2-dimethylamino-1-(4-morpholinophenyl)butanone-1, naphthalenesulfonyl chloride, N-phenylthioacridone, benzthiazole disulfide, triphenylwholphin, or a combination of a photo-reducing dye such as eosine or methylene blue and a reducing agent such as ascorbic acid or triethanolamine.

When the photosensitive glass powder-containing paste contains a polymer having a carboxyl group as a photosensitive polymer, solubility in an alkali aqueous solution during development is improved. The acid value of the polymer having a carboxyl group is preferably 50 to 150 mg KOH/g. When the acid value is 150 mg KOH/g or less, the development margin is widened. On the other hand, when the acid value is 50 mg KOH/g or more, solubility in an alkali aqueous solution is not reduced, and a fine pattern can be obtained.

The photosensitive glass powder-containing paste can be obtained by blending various kinds of components so as to achieve a predetermined composition, and then homogeneously mixing and dispersing the blend by three rollers or a kneader.

The viscosity of the photosensitive glass powder-containing paste can be appropriately adjusted according to the addition ratio of an inorganic powder, a thickener, an organic solvent, a polymerization inhibitor, a plasticizer, a precipitation preventive agent or the like, but it is preferably in the range of 2 to 200 Pa·s. For example, the viscosity is preferably 2 to 5 Pa·s when the photosensitive glass powder-containing paste is applied to a base material by a spin coating method, and the viscosity is preferably 10 to 50 Pa·s when the photosensitive glass powder-containing paste is applied to a base material by a blade coater method or a die coater method. When the photosensitive glass powder-containing paste is applied by a screen printing method once to obtain an applied film having a thickness of 10 to 20 μm, the viscosity is preferably 50 to 200 Pa·s.

The application step is a step of applying the glass powder-containing paste to the whole or a part of a surface of a base material to obtain an applied film. As the base material, a support having high heat resistance, such as a glass plate or a ceramic plate, can be used. The method for applying the glass powder-containing paste is, for example, a screen printing method, a bar coater, a roll coater, a die coater or a blade coater. The thickness of the resulting applied film can be adjusted according to the number of times of application, the mesh size of a screen, the viscosity of the paste, or the like.

The pattern forming step may include, for example, an exposure step of exposing the applied film obtained in the application step, through a photomask having a predetermined opening, and a development step of dissolving and removing a portion of the post-exposure applied film, which is soluble in a developer.

The exposure step is a step of photo-curing a necessary portion of the applied film by exposure or photo-decomposing an unnecessary portion of the applied film, so that an arbitrary portion of the applied film is soluble in a developer. The development step is a step of dissolving and removing a portion of the post-exposure applied film, which is soluble in a developer, with the developer to obtain a grid-like pre-firing pattern in which only a necessary portion remains.

In the exposure step, an arbitrary pattern may be directly drawn with laser light etc. without using a photomask. The exposure apparatus is, for example, a proximity exposure machine. The active light to be applied in the exposure step is, for example, near infrared light, visible light or ultraviolet light, and ultraviolet light is preferable. The light source is, for example, a low-pressure mercury lamp, a high-pressure mercury lamp, an ultra-high-pressure mercury lamp, a halogen lamp or a bactericidal lamp, and an ultra-high-pressure mercury lamp is preferable. Exposure conditions vary depending on the thickness of the applied film, but commonly the applied film is exposed for 0.01 to 30 minutes using an ultra-high-pressure mercury lamp with an output of 1 to 100 mW/cm$^2$.

The method for development in the development step is, for example, an immersion method, a spray method or a brush method. As the developer, a solvent capable of dissolving an unnecessary portion of the post-exposure applied film may be appropriately selected, but an aqueous solution containing water as a main component is preferable. For example, when the glass powder-containing paste contains a polymer having a carboxyl group, an alkali aqueous solution can be selected as the developer. The alkali aqueous solution is, for example, an inorganic alkali aqueous solution such as that of sodium hydroxide, sodium carbonate or potassium hydroxide, or an organic alkali aqueous solution such as that of tetramethylammonium hydroxide, trimethylbenzylammonium hydroxide or diethanolamine, and an organic alkali aqueous solution is preferable because it is easily removed in the firing step. The concentration of the alkali aqueous solution is preferably 0.05 to 5% by mass, more preferably 0.1 to 1% by mass. When the alkali concentration is less than 0.05% by mass, it may be unable to sufficiently remove an unnecessary portion of the post-exposure applied film. On the other hand, when the alkali concentration is more than 5% by mass, the grid-like pre-firing pattern may be peeled or corroded. The development temperature is preferably 20 to 50° C. for facilitating process control.

For forming a pattern by exposure and development, the glass powder-containing paste to be applied in the application step should be photosensitive. In other words, the glass powder-containing paste should contain a photosensitive organic component. The ratio of the organic component to the photosensitive glass powder-containing paste is preferably 30 to 80% by mass, more preferably 40 to 70% by mass. When the ratio of the organic component is less than 30% by mass, not only dispersibility of the inorganic component in the paste is deteriorated, so that defect easily occur in the firing step, but also the viscosity of the paste increases, so that coatability is deteriorated, and further stability of the paste is easily deteriorated. On the other hand, when the ratio of the organic component is more than 80% by mass, the shrinkage ratio of the grid-like pattern in the firing step increases, so that defects easily occur.

Preferably, the glass powder contained in the photosensitive glass powder-containing paste has a softening temperature of 480° C. or higher for almost completely removing the organic component in the firing step to secure the strength of the barrier rib that is finally obtained. When the softening temperature is lower than 480° C., there is the possibility that the glass powder is softened before the organic component is sufficiently removed in the firing step, so that the organic component remains in glass after sintering, and induces coloring of the barrier rib, leading to a reduction in luminance of the scintillator panel.

The firing step is a step of firing the grid-like pre-firing pattern, which is obtained in the pattern forming step, to dissolve and remove the organic component contained in the glass powder-containing paste, and softening and sintering the glass powder to obtain a grid-like post-firing pattern, i.e. the barrier rib. Firing conditions vary depending on the composition of the glass powder-containing paste and the type of the base material, and firing can be performed in a firing furnace in an atmosphere of, for example, air, nitrogen or hydrogen. The firing furnace is, for example, a batch-type firing furnace or a belt-type continuous firing furnace. The temperature of firing is preferably 500 to 1000° C., more preferably 500 to 800° C., still more preferably 500 to 700° C. When the firing temperature is lower than 500° C., the organic component is not sufficiently decomposed and removed. On the other hand, the firing temperature is higher than 1000° C., the base material that can be used is limited to a ceramic plate etc. having high heat resistance. The firing time is preferably 10 to 60 minutes.

An article obtained by packing a phosphor in cells separated by barrier ribs as described above may be used as a scintillator panel (here, the base material used serves as a substrate in the scintillator panel according to the present invention), or barrier ribs and a phosphor may be separated from a base material after press-packing, and placed on a separately provided substrate to complete a scintillator panel.

EXAMPLES

The present invention will be described further in detail below by way of examples and comparative examples, but the present invention is not limited to these examples.

(Method for Measuring Porosity)

A scintillator panel was cut in a direction vertical to a substrate, the cut surface was then abraded by an ion milling method to expose a cross-section vertical to the substrate, and an electrical conductivity imparting treatment (Pt coating) was performed to prepare a measurement sample. Thereafter, a cross-section image was obtained using a field emission☐type scanning electron microscope S-4800 (manufactured by Hitachi High-Technologies Corporation.). For the obtained image, a solid portion and a void portion were distinguished from each other by binarization, and the ratio of the void portion was determined by image analysis to measure the porosity. For minimizing a measurement error, the analyzed range of the image of a cross-section of the phosphor was prevented from including the barrier rib, the substrate or the like, image analysis was performed for each of 10 randomly selected cells, the analysis results were averaged, and the average thus obtained was defined as a porosity of the phosphor.

(Method for Determining Presence/Absence of Grain Boundary and Method for Measuring Average Particle Size)

A measurement sample was prepared in the same manner as in measurement of the porosity. Thereafter, a cross-section crystal orientation image was obtained by an EBSD method using JSM-6500F (manufactured by JEOL Ltd.) equipped with a DVC-type EBSD (manufactured by TSL Company). Using attached software, the obtained image was analyzed for three randomly selected cells to detect a crystal grain boundary of a phosphor as a closed boundary having an angle of 5 degrees or more, and it was determined that a grain boundary was present when a grain boundary was detected in the phosphor for each of the cells. The average particle size was calculated in terms of an area average particle size for crystal grains in the three cells using attached software. When a grain boundary was not present in the phosphor, the phosphor included in one cell was regarded as one particle, and the average particle size was calculated.

(Phosphor)

As powders of CsI:Tl, NaI:Tl and SrI2:Eu, those obtained by grinding commercially available phosphor single crystals in dry air, and causing the resulting particles to pass through a sieve to remove coarse particles. As GOS:Tb (gadolinium oxysulfide doped with Tb), a commercial product was used as it was.

(Raw Material of Glass Powder-Containing Paste)

Raw materials used for preparation of a photosensitive glass powder-containing paste are as follows.
Photosensitive monomer M-1: trimethylolpropane triacrylate
Photosensitive monomer M-2: tetrapropylene glycol dimethacrylate
Photosensitive polymer: polymer obtained by addition reaction of 0.4 equivalents of glycidyl methacrylate with a carboxyl group of copolymer of methacrylic acid/methyl methacrylate/styrene at a mass ratio of 40:40:30 (mass average molecular weight: 43000; acid value: 100).
Photo-polymerization initiator:
    2-benzyl-2-dimethylamino-1-(4-morpholinophenyl)butano ne-1(IC369; manufactured by BASF SE).
Polymerization inhibitor:
    1,6-hexanediol-bis[(3,5-di-t-butyl-4-hydroxyphenyl)propionate]).
Ultraviolet ray absorber solution: 0.3 mass % γ-butyrolactone solution of Sudan IV (manufactured by TOKYO OHKA KOGYO Co., Ltd.).
Viscosity modifier: FLOWNON EC121 (manufactured by KYOEISHA CHEMICAL Co., LTD).
Solvent: γ-butyrolactone.
Low-softening-point glass powder:
    $SiO_2$: 27% by mass, $B_2O_3$: 31% by mass, ZnO: 6% by mass, $Li_2O$: 7% by mass, MgO: 2% by mass, CaO: 2% by mass, BaO: 2% by mass, $Al_2O_3$: 23% by mass, refractive index (ng): 1.56, glass softening temperature; 588° C., thermal expansion coefficient: $70 \times 10^{-7}$ ($K^{-1}$), average particle size: 2.3 μm.
High-softening-point glass powder:
    $SiO_2$: 30% by mass, $B_2O_3$: 31% by mass, ZnO: 6% by mass, MgO: 2% by mass, CaO: 2% by mass, BaO: 2% by mass, $Al_2O_3$: 27% by mass, refractive index (ng): 1.55, softening temperature; 790° C., thermal expansion coefficient: $32 \times 10^{-7}$ ($K^{-1}$), average particle size: 2.3 μm.

(Preparation of Glass Powder-containing Paste)

4 parts by mass of a photosensitive monomer M-1, 6 parts by mass of a photosensitive monomer M-2, 24 parts by mass of a photosensitive polymer, 6 parts by mass of a photo-polymerization initiator, 0.2 parts by mass of a polymerization inhibitor and 12.8 parts by mass of an ultraviolet ray absorber solution were heated and dissolved in 38 parts by mass of a solvent at a temperature of 80° C. The obtained solution was cooled, and 9 parts by mass of a viscosity modifier was then added to obtain an organic solution 1. The obtained organic solution 1 was applied to a glass plate, and dried to obtain an organic coating film. The organic coating film had a refractive index (ng) of 1.555.

To 50 parts by mass of the organic solution 1 were added 40 parts by mass of a low-softening-point glass powder and 10 parts by mass of a high-softening-point glass powder, and the mixture was then kneaded by a three roll mill to obtain a glass powder-containing paste.

(Raw Materials of Reflecting Layer Paste)

Raw materials used for preparation of a reflecting layer paste are as follows.
Filler: titanium oxide (manufactured by Ishihara Sangyo Kaisha, Ltd.).
Binder solution: mixed solution of 5% by mass of ethyl cellulose (manufactured by The Dow Chemical Company) and 95% by mass of terpineol (Nippon Terpene Chemicals, Inc.).
Monomer: mixture of 30% by mass of dipentaerythritol pentaacrylate and 70% by mass of dipentaerythritol hexaacrylate (each manufactured by Toagosei Company, Limited).
Polymerization initiator:
    1,1'-azobis(cyclohexane-1-carbonitrile) (V-40; manufactured by Wako Pure Chemical Industries, Ltd.).

(Preparation of Reflecting Layer Paste)

50 parts by mass of a filler, 45 parts by mass of a binder solution, 4.5 parts by mass of a monomer and 1.5 parts by mass of a polymerization initiator were kneaded by a three roll mill to obtain a reflecting layer paste.

(Formation of Barrier Rib)

A soda glass plate having a size of 125 mm×125 mm×0.7 mm was used as a base material. The glass powder-containing paste was applied to a surface of the base material by a die coater so as to achieve a thickness of 500 µm after drying, and dried to obtain a glass powder-containing paste applied film. Next, using an ultra-high-pressure, the glass powder-containing paste applied film was exposed with an exposure amount of 500 mJ/cm$^2$ through a photomask (chromium mask having a pitch of 194 µm and a line width of 20 µm and having a grid-like opening), the photomask having an opening corresponding to a desired pattern. The applied film after exposure was developed in a 0.5 mass % ethanol amine aqueous solution, so that unexposed portion was removed to obtain a grid-like pre-firing pattern. The obtained grid-like pre-firing pattern was fired at 585° C. for 15 minutes in air to form grid-like barrier ribs containing glass as a main component. The porosity of the barrier rib was 2.5%, the height L1 of the barrier rib was 350 µm, the interval L2 between barrier ribs was 194 µm, the bottom part width L3 of the barrier rib was 35 µm, and the top part width L4 of the barrier rib was 20 µm, and the Young's modulus of the barrier rib was 20 GPa.

Example 1

0.11 g/cm$^2$ of a CsI:Tl powder was supplied onto a base material provided with grid-like barrier ribs, and was flattened by a squeegee, and put in a Nylon (registered trademark) bag together with the base material, and the opening of the bag was thermally welded to seal the bag. The bag was set in an isostatic pressure press apparatus (manufactured by Kobe Steel, Ltd.), and the powder was press-packed at a pressure of 400 MPa and a temperature of 25° C. to prepare a scintillator panel 1.

The CsI:Tl packed in cells had a grain boundary. The CsI:Tl packed in the cells had a porosity of 5% and an average particle size of 25 µm.

The prepared scintillator panel 1 was set in a FPD (PaxScan3030; manufactured by Varian Company) to prepare a radiation detector. The radiation detector was irradiated with an X-ray with a tube voltage of 60 kVp from the substrate side of the scintillator panel 1, and the amount of light emitted from a scintillator layer was detected by the FPD to evaluate the luminance of the scintillator panel 1. The image sharpness of the scintillator panel 1 was evaluated on the basis of a photographed image of a short wave chart. The scintillator panel 1 exhibited a good luminance and image sharpness.

Example 2

Except that in press-packing, the pressure was 60 MPa, and the temperature was 150° C., the same procedure as in Example 1 was carried out to prepare a scintillator panel, and evaluation was performed. The phosphor packed in cells of the obtained scintillator panel 2 had a grain boundary, and had a porosity of 2% and an average particle size of 35 µm. The luminance of the scintillator panel 2 was 110 in terms of a relative value where the luminance of the scintillator panel 1 is 100. Thus, the scintillator panel 2 exhibited a good luminance. The scintillator panel 2 also exhibited a good image sharpness.

Example 3

The reflecting layer paste was applied to a surface of a base material provided with grid-like barrier ribs, and was left standing for 5 minutes, and the deposited reflecting layer paste was then scraped off by a rubber squeegee with a hardness of 80°. Thereafter, drying was performed in hot air ovens at 80° C.° and 130° C. for 30 minutes each to form a reflecting layer on the surface of the barrier rib and on portions where the barrier rib was not formed. Thereafter, in the same manner as in Example 1, a CsI:Tl powder was supplied, and press-packed to prepare a scintillator panel 3, and evaluation was performed.

The phosphor packed in cells of the obtained scintillator panel 3 had a grain boundary, and had a porosity of 5% and an average particle size of 25 µm. The luminance of the scintillator panel 2 was 130 in terms of a relative value where the luminance of the scintillator panel 1 is 100. Thus, the scintillator panel 2 exhibited a good luminance. The scintillator panel 3 also exhibited a good image sharpness.

Example 4

In the same manner as in Example 3, a reflecting layer was formed on a surface of a base material provided with grid-like barrier ribs. Thereafter, 0.11 g/cm$^2$ of a CsI:Tl powder was supplied onto the base material, flattened by a squeegee, and put in a Nylon (registered trademark) bag together with the base material. Next, using a vacuum packaging machine (TOSPACK V-280; manufactured by TOSEI CORPORATION), the bag was evacuated for 30 seconds, and then thermally welded to be sealed. Thereafter, the same procedure as in Example 3 was carried out to prepare a scintillator panel 4, and evaluation was performed.

The phosphor packed in cells of the obtained scintillator panel 4 had a grain boundary, and had a porosity of 4% and an average particle size of 30 µm. The luminance of the scintillator panel 6 was 135 in terms of a relative value where the luminance of the scintillator panel 1 is 100. Thus, the scintillator panel 6 exhibited a good luminance. The scintillator panel 4 also exhibited a good image sharpness.

Example 5

A rubber sheet having a thickness of about 1 mm was bored by a size larger than a packing area to form a rubber frame, the rubber frame was placed on a SUS plate, and 0.11 g/cm$^2$ of a CsI:Tl powder was supplied, and leveled. Thereafter, the SUS plate, the rubber frame and the CsI:Tl powder were put in a Nylon (registered trademark) bag. Next, using a vacuum packaging machine (TOSPACK V-280; manufactured by TOSEI CORPORATION), the bag was evacuated for 30 seconds, and then thermally welded to be sealed. The bag was set in an isostatic pressure press apparatus (manufactured by Kobe Steel, Ltd.), and pressed at a pressure of 400 MPa and a temperature of 25° C. to prepare a CsI:Tl press-molded film 1.

In the same manner as in Example 3, a reflecting layer was formed on a surface of a base material provided with grid-like barrier ribs. Thereafter, the press-molded film 1 was supplied onto the base material, and put in a Nylon (registered trademark) bag together with the base material. Next, using a vacuum packaging machine (TOSPACK V-280; manufactured by TOSEI CORPORATION), the bag was evacuated for 30 seconds, and then thermally welded to be sealed. Thereafter, in the same manner as in Example 3, press-packing was performed to prepare a scintillator panel 5, and evaluation was performed.

The phosphor packed in cells of the obtained scintillator panel 5 had a grain boundary, and had a porosity of 3% and an average particle size of 30 µm. The luminance of the scintillator panel 6 was 140 in terms of a relative value where the luminance of the scintillator panel 1 is 100. Thus, the scintillator panel 6 exhibited a good luminance. The scintillator panel 5 also exhibited a good image sharpness.

Example 6

On a surface of a base material provided with grid-like barrier ribs, an aluminum film was formed in a thickness of 0.4 μm by a sputtering method to form a light shielding layer. Thereafter, in the same manner as in Example 5, the press-molded film 1 was press-packed to prepare a scintillator panel 6, and evaluation was performed.

The phosphor packed in cells of the obtained scintillator panel 6 had a grain boundary, and had a porosity of 3% and an average particle size of 30 μm. The luminance of the scintillator panel 6 was 80 in terms of a relative value where the luminance of the scintillator panel 1 is 100. Thus, the scintillator panel 6 exhibited a relatively good luminance. The scintillator panel 6 exhibited an extremely good image sharpness.

Example 7

In the same manner as in Example 3, a reflecting layer was formed on a surface of a base material provided with grid-like barrier ribs. On the base material after formation of the reflecting layer, a polyparaxylylene film was formed in a thickness of 4 μm by vapor deposition polymerization to form a protective layer. Thereafter, in the same manner as in Example 5, the press-molded film 1 was press-packed to prepare a scintillator panel 7, and evaluation was performed.

The phosphor packed in cells of the obtained scintillator panel 7 had a grain boundary, and had a porosity of 3% and an average particle size of 30 μm. The luminance of the scintillator panel 7 was 150 in terms of a relative value where the luminance of the scintillator panel 1 is 100. Thus, the scintillator panel 7 exhibited a good luminance. The scintillator panel 7 also exhibited a good image sharpness.

Example 8

In the same manner as in Example 6, a light shielding layer was formed on a surface of a base material provided with grid-like barrier ribs. Next, in the same manner as in Example 3, a reflecting layer was formed on the base material provided with the light shielding layer. Further, in the same manner as in Example 7, a protective layer was formed on the base material provided with the light shielding layer and the reflecting layer. Thereafter, in the same manner as in Example 5, the press-molded film 1 was press-packed to prepare a scintillator panel 8, and evaluation was performed.

The phosphor packed in cells of the obtained scintillator panel 8 had a grain boundary, and had a porosity of 3% and an average particle size of 30 μm. The luminance of the scintillator panel 8 was 130 in terms of a relative value where the luminance of the scintillator panel 1 is 100. Thus, the scintillator panel 8 exhibited a good luminance. The scintillator panel 6 exhibited an extremely good image sharpness.

Example 9

Except that in press-packing, the pressure was 200 MPa, and the temperature was 150° C., the same procedure as in Example 5 was carried out to prepare a scintillator panel 9, and evaluation was performed.

The phosphor packed in cells of the obtained scintillator panel 9 had a grain boundary, and had a porosity of 0.6% and an average particle size of 45 μm. The luminance of the scintillator panel 9 was 150 in terms of a relative value where the luminance of the scintillator panel 1 is 100. Thus, the scintillator panel 9 exhibited a good luminance. The scintillator panel 9 also exhibited a good image sharpness.

Example 10

Except that the medium was changed to metal foil capsule having a thickness of 100 μm (sealed by a metal foil capsule sealing apparatus (Kobe Steel, Ltd.) as a packaging bag used in press-packing, the press pressure was 400 MPa, and the temperature was 300° C., the same procedure as in Example 5 was carried out to prepare a scintillator panel 10, and evaluation was performed.

The phosphor packed in cells of the obtained scintillator panel 10 had a grain boundary, and had a porosity of 0.2% and an average particle size of 50 μm. The luminance of the scintillator panel 10 was 150 in terms of a relative value where the luminance of the scintillator panel 1 is 100. Thus, the scintillator panel 10 exhibited a good luminance. The scintillator panel 10 also exhibited a good image sharpness.

Example 11

Except that in press-packing, the pressure was 400 MPa, and the temperature was 550° C., the same procedure as in Example 10 was carried out to prepare a scintillator panel 11, and evaluation was performed.

The phosphor packed in cells of the obtained scintillator panel 11 had a grain boundary, and had a porosity of 0% and an average particle size of 55 μm. The luminance of the scintillator panel 11 was 140 in terms of a relative value where the luminance of the scintillator panel 1 is 100. Thus, the scintillator panel 11 exhibited a good luminance although the luminance was slightly lower as compared to Example 10. The scintillator panel 11 also exhibited a good image sharpness.

Example 12

Except that in press-packing, the pressure was 50 MPa, and the temperature was 25° C., the same procedure as in Example 5 was carried out to prepare a scintillator panel 12, and evaluation was performed.

The phosphor packed in cells of the obtained scintillator panel 12 had a grain boundary, and had a porosity of 20% and an average particle size of 10 μm. The luminance of the scintillator panel 12 was 105 in terms of a relative value where the luminance of the scintillator panel 1 is 100. Thus, the scintillator panel 12 exhibited a good luminance although the luminance was lower as compared to Example 5. The scintillator panel 12 also exhibited a good image sharpness.

Example 13

Except that in press-packing, the pressure was 100 MPa, and the temperature was 25° C., the same procedure as in Example 5 was carried out to prepare a scintillator panel 13, and evaluation was performed.

The phosphor packed in cells of the obtained scintillator panel 13 had a grain boundary, and had a porosity of 8% and an average particle size of 20 μm. The luminance of the scintillator panel 13 was 120 in terms of a relative value where the luminance of the scintillator panel 1 is 100. Thus, the scintillator panel 13 exhibited a good luminance. The scintillator panel 13 also exhibited a good image sharpness.

Example 14

Except that in press-packing, the pressure was 980 MPa, and the temperature was 25° C., the same procedure as in Example 5 was carried out to prepare a scintillator panel 14, and evaluation was performed.

The phosphor packed in cells of the obtained scintillator panel 14 had a grain boundary, and had a porosity of 2% and an average particle size of 25 μm. The luminance of the scintillator panel 14 was 130 in terms of a relative value where the luminance of the scintillator panel 1 is 100. Thus, the scintillator panel 14 exhibited a good luminance. The scintillator panel 14 exhibited a relatively good image sharpness although the sharpness was slightly deteriorated as compared to Example 5. The cause of the deterioration of the image sharpness may be damage to a part of barrier ribs due to packing at a high pressure.

Example 15

Except that NaI:Tl was used as a phosphor, and the supply amount of the phosphor in preparation of a press-molded film was 0.09 g/cm$^2$, the same procedure as in Example 5 was carried out to prepare a scintillator panel 15, and evaluation was performed.

The phosphor packed in cells of the obtained scintillator panel 15 had a grain boundary, and had a porosity of 3% and an average particle size of 30 μm. The luminance of the scintillator panel 15 was 130 in terms of a relative value where the luminance of the scintillator panel 1 is 100. Thus, the scintillator panel 15 exhibited a good luminance. The scintillator panel 15 also exhibited a good image sharpness.

Example 16

Except that SrI$_2$:Eu was used as a phosphor, and the supply amount of the phosphor in preparation of a press-molded film was 0.14 g/cm$^2$, the same procedure as in Example 5 was carried out to prepare a scintillator panel 16, and evaluation was performed.

The phosphor packed in cells of the obtained scintillator panel 16 had a grain boundary, and had a porosity of 3% and an average particle size of 30 μm. The luminance of the scintillator panel 16 was 160 in terms of a relative value where the luminance of the scintillator panel 1 is 100. Thus, the scintillator panel 16 exhibited a good luminance. The scintillator panel 16 also exhibited a good image sharpness.

Comparative Example 1

Except that 0.11 g/cm$^2$ of GOS:Tb was used as a phosphor, the same procedure as in Example 1 was carried out to prepare a scintillator panel 17, and evaluation was performed. The GOS:Tb packed in cells of the obtained scintillator panel 17 had a grain boundary, and had a porosity of 40% and an average particle size of 10 μm. The luminance of the scintillator panel 17 was 70 in terms of a relative value where the luminance of the scintillator panel 1 is 100. Thus, the scintillator panel 17 was poor in luminance. Since the scintillator panel 17 had a high porosity, emitted light was excessively scattered, and thus the scintillator panel 17 was also poor in image sharpness.

Comparative Example 2

0.11 g/cm$^2$ of a CsI:Tl powder was supplied onto a base material provided with grid-like barrier ribs, and was flattened by a squeegee. Thereafter, the temperature was elevated to 630° C. under reduced pressure, so that the CsI:Tl was melted, and packed in cells to prepare a scintillator panel 18, and evaluation was performed. The CsI:Tl packed in the cells of the obtained scintillator panel 18 had no grain boundary, and had a porosity of 1.3%. The luminance of the scintillator panel 18 was 50 in terms of a relative value where the luminance of the scintillator panel 1 is 100. Thus, the scintillator panel 18 was poor in luminance. The barrier ribs were partially melted and deformed due to elevation of the temperature to 630° C., and therefore the scintillator panel 18 was also poor in image sharpness.

Comparative Example 3

Except that in press-packing, the pressure was 5 MPa, and the temperature was 25° C., the same procedure as in Example 1 was carried out to prepare a scintillator panel 19, and evaluation was performed.

The phosphor packed in cells of the obtained scintillator panel 19 had a grain boundary, and had a porosity of 30% and an average particle size of 10 μm. The luminance of the scintillator panel 9 was 60 in terms of a relative value where the luminance of the scintillator panel 1 is 100. Thus, the scintillator panel 9 was poor in luminance. Since the scintillator panel 19 had a high porosity, emitted light was excessively scattered, and thus the scintillator panel 19 was also poor in image sharpness.

From the above results, it is evident that the scintillator panel according to the present invention contributes to marked improvement of the luminance and image sharpness of a scintillator panel in a radiation detector.

The present invention can be advantageously used as a scintillator panel that forms a radiation detector to be used in a medical diagnosis apparatus, nondestructive inspection equipment or the like.

DESCRIPTION OF REFERENCE SIGNS

1: Radiation detector
2: Scintillator panel
3: Output substrate
4: Substrate
5: Barrier rib
6: Phosphor layer
7: Barrier layer
8: Photoelectric conversion layer
9: Output layer
10: Substrate
11: Power supply unit
12: Light shielding layer
13: Reflecting layer
14: Protective layer

The invention claimed is:

1. A scintillator panel comprising: a substrate; barrier ribs placed on the substrate; and a phosphor packed into cells separated by the barrier ribs, the phosphor being a compound selected from the group consisting of CsI:Tl, NaI:Tl and SrI2:Eu, the phosphor having a porosity of 20% or less and having a grain boundary, wherein the phosphor has an average particle size of 20 to 200 μm, and wherein the grain boundary is a discontinuous boundary surface generated between a plurality of crystals of the phosphor by observing a cross-section of the phosphor using EBSD (electron back scatter diffraction patterns) method.

2. The scintillator panel according to claim 1, wherein the phosphor has a porosity of 0.1% or more.

3. The scintillator panel according to claim 1, wherein the barrier rib includes an inorganic substance, and the barrier rib has a porosity of 25% or less.

4. The scintillator panel according to claim 1, wherein the barrier rib has a Young's modulus of 10 GPa or more.

5. The scintillator panel according to claim 1, wherein the barrier rib contains glass as a main component.

6. The scintillator panel according to claim 1, wherein the scintillator panel includes a reflecting layer between the barrier rib and the phosphor, and the reflecting layer contains a metal oxide as a main component.

7. The scintillator panel according to claim 1, wherein the scintillator panel includes a light shielding layer between the barrier rib and the phosphor, and the light shielding layer contains a metal as a main component.

8. The scintillator panel according to claim 6 or 7, wherein the scintillator panel includes a protective layer between the reflecting layer and the phosphor or between the light shielding layer and the phosphor.

9. The scintillator panel according to claim 1, which is manufactured by a method including the step of press-packing a phosphor selected from the group consisting of CsI:Tl, NaI:Tl and SrI2:Eu in cells separated by barrier ribs.

10. The scintillator panel according to claim 9, wherein the pressure in the press-packing is 10 to 1000 MPa.

11. The scintillator panel according to claim 9 or 10, wherein the temperature in the press-packing is 0 to 630° C.

12. The scintillator panel according to claim 9, wherein the press-packing is performed under vacuum.

13. The scintillator panel according to claim 9, wherein the phosphor that is subjected to the press-packing step is in the form of a thin-film.

14. The scintillator panel according to claim 13, wherein the phosphor in the form of a thin-film is obtained by press-molding a phosphor powder.

15. A radiation detector comprising the scintillator panel according to claim 1.

* * * * *